(12) United States Patent
Jasperse

(10) Patent No.: US 11,287,367 B2
(45) Date of Patent: Mar. 29, 2022

(54) SYSTEM AND METHOD FOR OPTICAL WHOLE BLOOD HEMOLYSIS DETECTION

(71) Applicant: Siemens Healthcare Diagnostics Inc., Tarrytown, NY (US)

(72) Inventor: Jeffrey Jasperse, Newton, MA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 675 days.

(21) Appl. No.: 16/317,993

(22) PCT Filed: Jun. 7, 2017

(86) PCT No.: PCT/US2017/036338
§ 371 (c)(1),
(2) Date: Jan. 15, 2019

(87) PCT Pub. No.: WO2018/017199
PCT Pub. Date: Jan. 25, 2018

(65) Prior Publication Data
US 2021/0285868 A1      Sep. 16, 2021

Related U.S. Application Data

(60) Provisional application No. 62/363,584, filed on Jul. 18, 2016.

(51) Int. Cl.
| | |
|---|---|
| *G01N 33/48* | (2006.01) |
| *G01N 21/25* | (2006.01) |
| *G01N 1/14* | (2006.01) |
| *G01N 1/28* | (2006.01) |
| *G01N 33/49* | (2006.01) |
| *G06V 20/69* | (2022.01) |

(52) U.S. Cl.
CPC ............... *G01N 21/25* (2013.01); *G01N 1/14* (2013.01); *G01N 1/286* (2013.01); *G01N 33/49* (2013.01); *G06V 20/69* (2022.01)

(58) Field of Classification Search
CPC .... G01N 33/49; G01N 15/05; G01N 15/1434; A61B 5/14532; A61B 5/1455
USPC .......................................................... 356/39
See application file for complete search history.

(56) References Cited

U.S. PATENT DOCUMENTS

| | | |
|---|---|---|
| 4,764,021 A | 8/1988 | Eppes |
| 6,172,744 B1 | 1/2001 | Scharlack et al. |
| 6,219,132 B1 | 4/2001 | Scharlack et al. |

(Continued)

FOREIGN PATENT DOCUMENTS

| | | |
|---|---|---|
| AU | 2013205504 A1 | 5/2013 |
| WO | 2015124512 A1 | 8/2015 |

OTHER PUBLICATIONS

International Search Report and Written Opinion of International Application No. PCT/US2017/036338 dated Sep. 6, 2017.

(Continued)

*Primary Examiner* — Md M Rahman
(74) *Attorney, Agent, or Firm* — Dunlap Codding, P.C.

(57) ABSTRACT

A method and system is described that includes obtaining a whole blood sample and obtaining a first light absorbance profile of the whole blood sample. Next, the whole blood sample is hemolyzed to generate a hemolyzed sample of blood and a second light absorbance profile of the hemolyzed sample of blood is obtained. The level of hemolysis in the whole blood sample is determined by comparing the first light absorbance profile and the second light absorbance profile.

16 Claims, 12 Drawing Sheets

(56) References Cited

U.S. PATENT DOCUMENTS

| | | |
|---|---|---|
| 6,262,798 B1 | 7/2001 | Shepherd et al. |
| 2002/0167667 A1 | 11/2002 | Samsoondar et al. |
| 2007/0244382 A1 | 10/2007 | Robinson et al. |
| 2010/0150779 A1 | 6/2010 | Chow et al. |
| 2010/0159500 A1 | 6/2010 | Schlaminger |
| 2015/0294461 A1 | 10/2015 | Satish et al. |

OTHER PUBLICATIONS

European Search Report and Written Opinion of European Application No. 17831471.2 dated Apr. 29, 2019.
Neudel et al,"Effect of hemolysis on oxygen and hematocrit measurements by near infrared reflectance spectroscopy"; May 1, 2002 (May 1, 2002), A Medical Engineering & Physics, vol. 24, No. 4, pp. 301-307.
Dolci et al., Harmonization of automated hemolysis index assessment and use: Is it possible?, 2014, Clinica Chimica Acta, vol. 432, pp. 38-43.

SYSTEM AND METHOD FOR OPTICAL WHOLE BLOOD HEMOLYSIS DETECTION

CROSS-REFERENCE TO RELATED APPLICATIONS

The present application claims the benefit of and priority to U.S. Provisional Application Ser. No. 62/363,584, filed Jul. 18, 2016, the entire disclosure of which is incorporated by reference into the present application.

FIELD OF THE DISCLOSURE

The present disclosure relates to the optical detection and determination of hemolysis levels based on analysis of a whole blood sample.

BACKGROUND

Patient blood samples used in diagnostic tests, such as blood gas and co-oximetry (co-ox) analyzers, often are hemolyzed during the process of acquiring the sample from the patient, e.g. during venipuncture draw. Blood samples may also be hemolyzed due to blood illnesses, e.g., sickle cell anemia. Accurately attributing the cause of hemolysis in blood samples in diagnostic tests is important because hemolysis caused by blood illness, if diagnosed early, can possibly improve clinical patient outcomes, e.g. by ordering another blood draw to identify a potential illness.

Hemolysis is a common problem that may introduce undesirable components into the plasma fraction of blood. Hemolysis refers to the rupturing of erythrocytes (red blood cells) and the release of their contents; including hemoglobin, potassium, magnesium, and lactate, into surrounding fluid (e.g., blood plasma). If hemolysis occurs on the sample to be measured, the extracellular components in the sample cause interference in a number of tests, leading to reduced measurement accuracy, and false positives or false negatives. For example, if the blood sample is hemolyzed to a high degree the potassium concentration will not reflect the potassium levels in plasma, potentially resulting in a false positive result. Elevated potassium not due to hemolysis can be an indicator of severe illness that can lead to death.

Healthcare professionals would benefit from knowing to what degree whole blood samples are hemolyzed and thus the reliability of the results of the diagnostic tests performed on whole blood samples. Hemolysis detection is widely and commonly performed on plasma or serum extracted from the original whole blood samples by means of centrifugation or filtration. To date, optical-based analyzers only perform hemolysis detection on plasma or serum and not on a whole blood sample. While there are analyzers that measure co-oximtetry analytes from whole blood samples, such as the RapidPoint 500® by Siemens Healthcare Diagnostics, Inc., separating the plasma from the whole blood to perform hemolysis detection adds complexity, increases service maintenance intervals, and reduces reliability, and adds considerable expense to such analyzers. Furthermore, the plasma based sample analyzers perform chemical reactions on the plasma that produce absorbance signals proportional to the constituent of interest at only a few specific wavelengths; plasma is a relatively clear fluid, hence the absorbance signals are far easier to measure compared to whole blood co-oximetry measurements.

SUMMARY

There is need to determine hemolysis levels on whole blood samples. An embodiment of the present disclosure is a method. The method includes obtaining a whole blood sample. The method may include obtaining a first light absorbance profile of the whole blood sample. The method also includes hemolyzing the whole blood sample to generate a hemolyzed sample of blood and obtaining a second light absorbance profile of the hemolyzed sample of blood. The method includes determining a level of hemolysis in the whole blood sample by comparing the first light absorbance profile and the second light absorbance profile.

Another embodiment of the present disclosure is a system for analyzing components of whole blood. The system includes a detection unit for obtaining a first light absorbance profile of a whole blood sample and a second light absorbance profile of a hemolyzed sample of blood. The system also includes a hemolyzer for hemolyzing the whole blood sample into the hemolyzed sample of blood. The system also includes a computer processor in communication with the detection unit, the computer processor configured to execute instructions that determine a level of hemolysis of the whole blood by comparing the first light absorbance profile of the whole blood sample to the second light absorbance profile of the hemolyzed sample.

BRIEF DESCRIPTION OF THE DRAWINGS

The foregoing summary, as well as the following detailed description of the illustrative embodiments of the present application, will be better understood when read in conjunction with the appended drawings. For the purposes of illustrating the present application, there is shown in the drawings illustrative embodiments of the disclosure. It should be understood, however, that the application is not limited to the precise arrangements and instrumentalities shown. In the drawings.

DETAILED DESCRIPTION OF THE INVENTIVE CONCEPTS

Figure 1A:
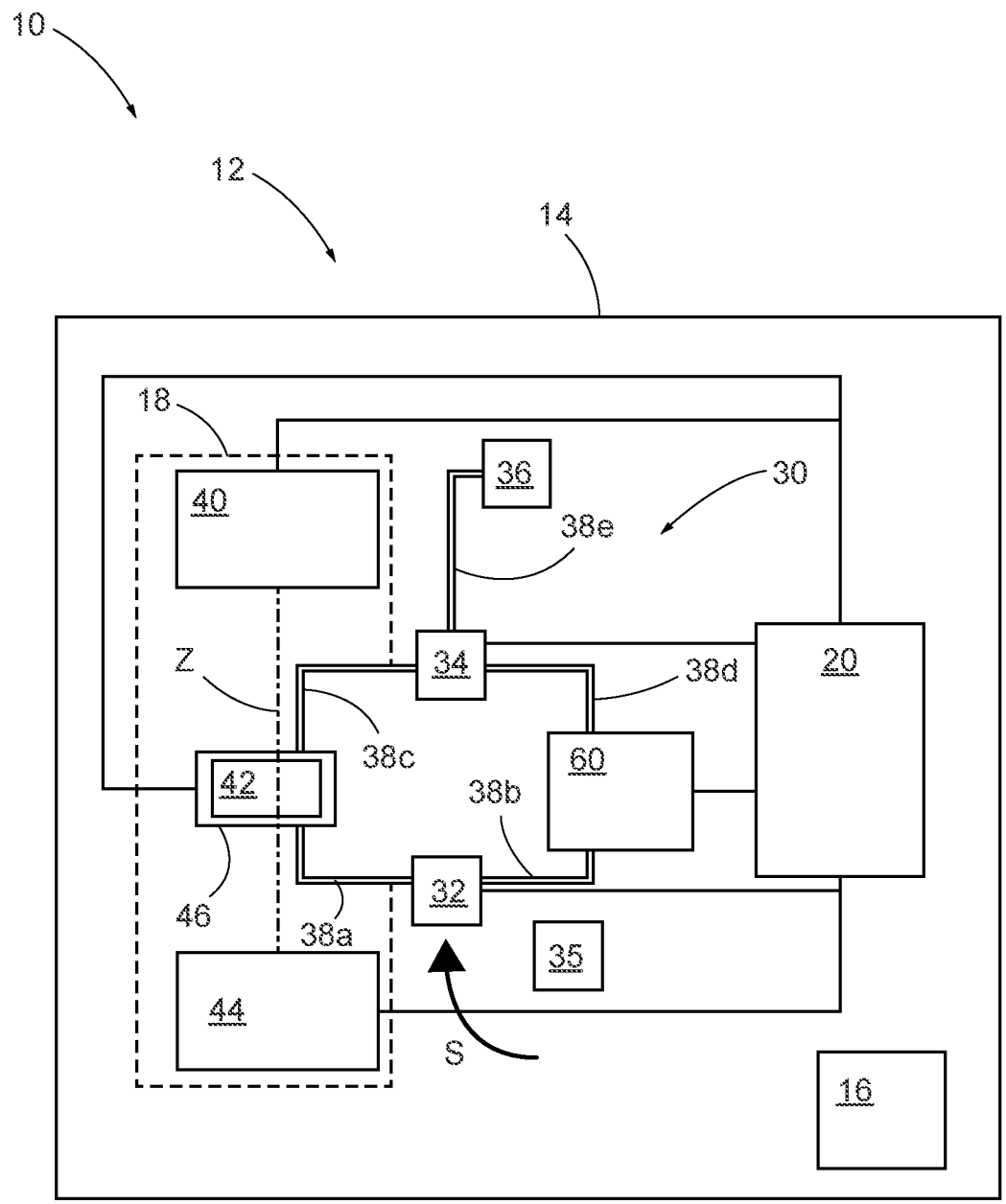
FIG. 1A is a schematic of a sample analyzer system according to an embodiment of the present disclosure.

Referring to FIG. 1A, an embodiment of the present disclosure is a sample analysis system 10 having a sample analyzer 12 that implements optical methods and techniques for analyzing hemolysis levels of a whole blood sample S. Hemolysis levels determined from a whole blood sample may be used to flag samples if hemolysis levels are within a predetermined range or reject samples that have too high of a hemolysis level. This is done, in part, because other measurements that may be affected by the hemolysis level in the whole blood sample. The hemolysis detection as described herein obviates the need of filtration and centrifuges used to separate plasma from the whole blood sample in order to detect hemolysis from the plasma fraction. Accordingly, the system, methods, and techniques described herein improve blood sample analysis using a less complex system than is otherwise available to date. The sample analysis system 10 may be suitable for point-of-care (POC) testing, which typically occurs at the site of patient care, such as in an emergency room. However, the sample analysis system 10 may be used in other clinical or laboratory settings not typically associated with POC testing.

Continuing with FIG. 1A, the sample analysis system 10 may include a sample holder 42 for carrying and/or holding a sample for analysis by the sample analyzer 12. The sample holder 42 may be a cartridge of multiple sample vessels, a single vessel, sample tube, strip and/or any other structure that can carrying and/or hold a sample. The sample holder 42 may interface with components of the sample analyzer 12 such that a user can insert the sample holder 42 containing the sample S into the sample analyzer 12. Alternatively, the sample holder 42 is adapted to receive a sample from a dispensing device (not shown).

The sample analyzer 12 includes a housing 14 and a mechanical stage (not shown) in the housing 14 that supports various components of the sample analyzer 12. The sample analyzer 12 includes a detection unit 18 for analyzing the sample contained in a sample holder 42, a hemolyzer 60, a fluid handling unit 30 for routing a sample between the sample holder 42 and the hemolyzer 60, and a computing device 20 that controls operation of various components of the sample analyzer 12. The computing device 20 is in electronic communication with the detection unit 18, the fluid handling unit 30, and the hemolyzer 60. A power source 16 powers components of the sample analyzer 12.

Figure 1B:
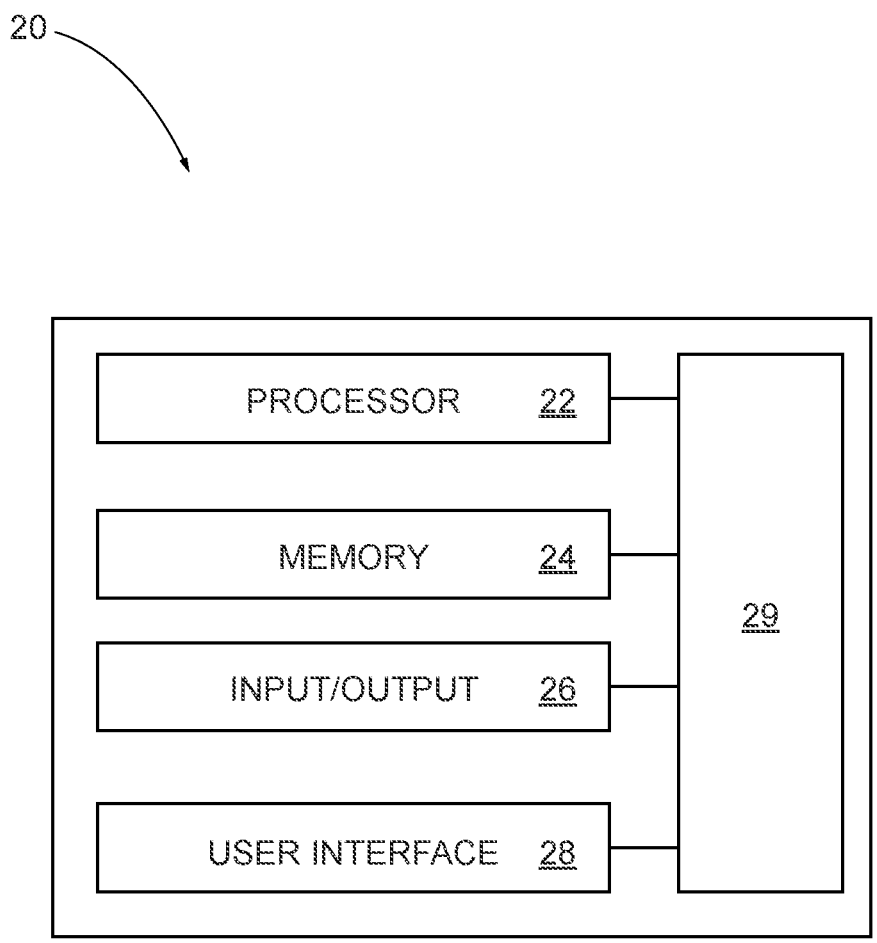
FIG. 1B is a schematic diagram of a computing device used to control operation of various aspects of the sample analyzer system shown in FIG. 1A.
Figure 2:
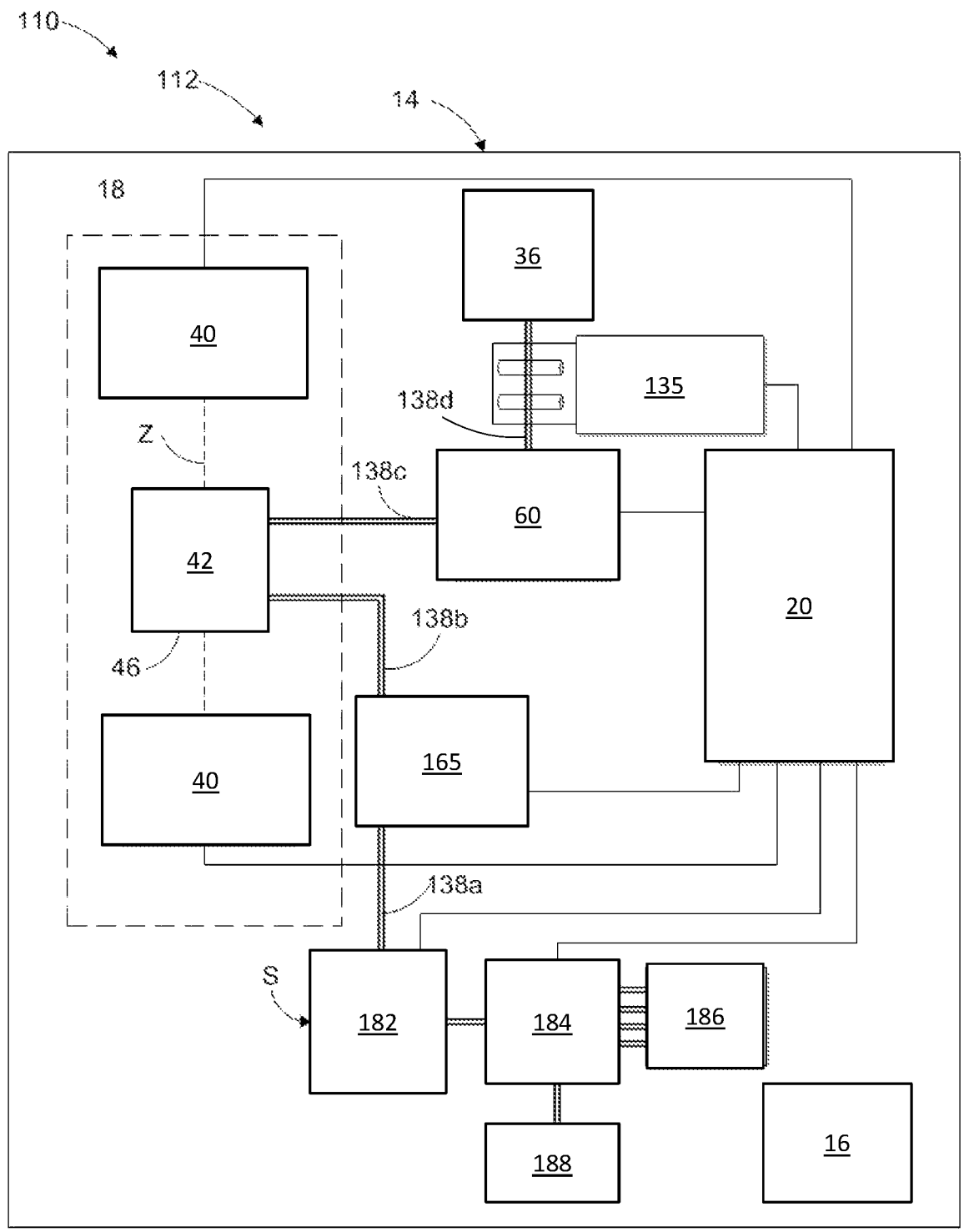
FIG. 2 is a schematic of a sample analyzer system according to another embodiment of the present disclosure.

The sample analyzer 12 may include additional components that are not shown in FIGS. 1 and 2. For example, the sample analyzer 12 may include a thermal plate for incubating the sample in the sample holder 42, a sample dispensing device to dispense a sample from a sample vial, and/or reagent, into the sample holder 42 as discussed above. Such a dispensing device may include components known to persons of skill in the art. The sample analyzer 12 may include a vacuum port to control pressure in the housing 14. In certain alternative embodiments for sample analyzers adapted to analyze whole blood and plasma and/or serum samples. The additional components described above are optional and sample analyzer 12 may not require them in order to implement the inventive concepts disclosed herein. However, the additional components may be implemented in a sample analyzer 12 as needed.

Referring to FIG. 1A, the detection unit 18 includes an illuminator 40 that emits a light along an optical axis Z, a sample holder 42 adjacent to the illuminator 40 and aligned with the optical axis Z, and a detector 44 adjacent to the support 46. A support 46 positions the sample holder 42 along the optical axis Z. The detection unit 18 includes a lens adjacent the illuminator, a filter, and a polarizer. The lens, filter and polarizer are not shown. On the opposite side of the support 46 is an optional linear polarizer. The illuminator 40 emits the light signal into the sample S, which absorbs portions of the light signal. The detector 44 detects components of the light signal not absorbed by sample S that exits sample holder 42 as further described below. The illuminator 40 is adapted to emit a light signal of specified wavelength, multiple wavelengths, or a full spectrum, into the sample S contained in the sample holder 42. In accordance with the illustrated embodiment, the illuminator 40 is a LED with an output from 450 nm to 700 nm. However, other light sources could be used. The sample holder 42 may designed to provide a path length between about 0.05 mm to about 0.08 mm. However, the path length may fall outside of this range as needed. The path length may vary outside of this range based on the desired accuracy and signal precision. The support 46 holds the sample holder 42 along the optical axis Z and may include a first aperture (or input aperture) adjacent to illuminator 40 and a second aperture (or output aperture) opposite the first aperture and that is adjacent to the detector 44. The first aperture and the second aperture are aligned along the optical axis Z such that light emitted from the illuminator 40 can pass through the first aperture into the sample holder 42. The detector 44 may be a spectrophotometer as is known in the art. In one example, the detector 44 may include an array of sensors configured to detect non-absorbed components of the light signal.

As shown in FIG. 1A, the fluid handling unit 30 includes a first valve 32, a second valve 34, a pump 35, and multiple conduits 38a-38e for routing fluid sample between the sample holder 42 to the hemolyzer 60 and/or to waste storage 36. The pump 35 pumps the sample through the conduits 38a-38e and valves 32 and 34. Conduit 38a couples the first valve 32 to the input side of the sample holder 42. Conduit 38b couples the hemolyzer 60 to the first valve 32. The second valve 34 is disposed along a conduit 38c at the output side of the sample holder 42. Conduit 38d couples the second valve 34 and the hemolyzer 60. Waste conduit 38e extends from the second valve 34 to waste storage 36. As further detailed below, whole blood S can be input to the sample holder 42 from a vessel, pipette, cartridge, or dispensing unit. The second valve 34 directs the whole blood sample S from the sample holder 42 to the hemolyzer 60. The first valve 32 directs the hemolyzed sample from the hemolyzer 60 to the sample holder 42. Furthermore, the second valve 34 may direct a hemolyzed sample that has been analyzed by the detection unit 18 to waste storage 36. The computing device 20 controls operation of the fluid handling unit 30 to facilitate analysis of the whole blood sample and the subsequent analysis of the hemolyzed sample.

The hemolyzer 60 is a device used to cause hemolysis of the whole blood sample S. The hemolyzer may be a mechanical hemolyzer whereby mechanical agitation of the whole blood sample S lyses the sample. In one example, the mechanical hemolyzer is reagent free. Specifically, the hemoglobin constituents exit the cellular walls of the red blood cells and enter the surrounding fluid. Alternatively and/or additionally, the hemolyzer 60 may be a chemical hemolyzer whereby an agent added to the whole blood sample S ruptures the cell wall, causing hemoglobin, among other constituents, to enter the surrounding fluid. For example, chemical lysing may include adding potassium ferricyanide to the sample.

FIG. 1B is an exemplary computing device 20 used to control operation of various aspect of the sample analyzer 12. The computing device 20 is configured to receive, process, and store information used to implement one or more software applications, such as software application 29. The software application 29 may include native instructions for operation of the sample analyzer 12 and instructions for determining the level of hemolysis in a whole blood sample S. Furthermore, in an alternative embodiment, the software application 29 may include instructions used to correct sample data based on the determined level of hemolysis of the whole blood sample. The hardware components of computing device 20 include any appropriate device, examples of which include a portable computing device, such as a laptop, tablet or smart phone, or other computing devices, such as a desktop computing device or a server-computing device that are coupled to the sample analyzer 12. Alternatively, various hardware components may be integrated with the sample analyzer 12 as a contained unit.

As illustrated in FIG. 1B, the computing device 20 includes one or more processor 22, a memory 24, input/output elements 26, and a user interface (UI) 28. It is emphasized that the operation diagram depiction of the computing device 20 is exemplary and is not intended to imply a specific implementation and/or configuration. The processor 22, memory 24, input/output portion 26 and user interface 28 can be coupled together to allow communications there between, and can interface with the software application 29. The software application 29 may include an application programmatic interface (API).

Continuing with FIG. 1B, the memory 24 can be volatile (such as some types of RAM), non-volatile (such as ROM, flash memory, etc.), or a combination thereof, depending upon the exact configuration and type of processor 22. The computing device 20 can include additional storage (e.g., removable storage and/or non-removable storage) including, but not limited to, tape, flash memory, smart cards, CD-ROM, digital versatile disks (DVD) or other optical storage, magnetic cassettes, magnetic tape, magnetic storage or other magnetic storage devices, universal serial bus (USB) compatible memory, or any other medium which can be used to store information and which can be accessed by the computing device 20.

Continuing with FIG. 1B, in various embodiments, the input/output portion 26 includes an antenna, lead or trace, electronic connector for wired connection, or a combination thereof. In some implementations, input/output portion 26 can include a receiver and transmitter, transceiver or transmitter-receiver. The input/output portion 26 is capable of receiving and/or providing information concerning components of the sample analyzer 12, such as the detection unit 18, fluid handling unit 30, and/or the hemolyzer 60. Furthermore, the input/output portion 26 is capable of receiving and/or providing information pertaining to communication with a network such as, for example, the Internet. As should be appreciated, transmit and receive functionality may also be provided by one or more devices external to computing device 20.

Referring to FIG. 1B, the user interface 28 can include an input device and/or display (input device and display not shown) that allows a user to communicate with or provide input instructions to the sample analyzer 12 and/or the computing device 20. The user interface 28 can include inputs that provide the ability to control the sample analyzer 12, via, for example, buttons, soft keys, a mouse, voice actuated controls, a touch screen, visual cues (e.g., moving a hand in front of a camera on the sample analyzer 12), or the like. The user interface 28 can provide outputs, including visual displays of the data obtained with the detection unit 18. Other outputs can include audio information (e.g., via speaker), mechanically (e.g., via a vibrating mechanism), or a combination thereof. In various configurations, the user interface 28 can include a display, a touch screen, a keyboard, a mouse, an accelerometer, a motion detector, a speaker, a microphone, a camera, or any combination thereof. The user interface 28 can further include any suitable device for inputting biometric information, such as, for example, fingerprint information, retinal information, voice information, and/or facial characteristic information, for instance, so as to require specific biometric information for access to the computing device 20. It should be appreciated that the computer devices can operate via any suitable operating system, such as Android, BSD, iOS, Linux, OS X, QNX, Microsoft Windows, Windows Phone, and IBM z/OS. Furthermore, the software application can operate with any of the aforementioned operation systems.

The sample analyzer 12 may also be adapted to obtain other measurements (in addition to hemolysis levels) from a whole blood sample. For example, the sample analyzer 12 may be adapted to measure co-oximetry analytes. An exemplary sample analyzer used to measure Co-oximetry analytes is the RAPIDPoint 500® marketed by Siemens Healthcare Diagnostics Inc. The RAPIDPoint 500 is a blood gas analyzer that measures co-oximetry analytes in whole blood using ion selective membrane (ISE) sensors. The sensors may be potentiometric, amperometic, and conductiometric type sensors. Alternatively, the sensors may be considered metabolite, electrolyte, and gas analyte sensors. This exemplary analyzer has a spectrophotometer that measures co-oximetry analytes of the sample in an optical chamber. Alternatively, the sample analyzer 12 may be adapted to obtain measurements from a whole blood sample as described above in addition to measurement from other liquid samples, such as plasma or serum.

FIG. 2 illustrates an alternative embodiment of a sample analysis system 110 and sample analyzer 112 used to determine hemolysis levels in whole blood samples. The embodiment of the sample analyzer 112 illustrated in FIG. 2 is similar to the embodiment of the sample analyzer illustrated in FIG. 1B. Accordingly, similar reference numbers are used to identify elements of the sample analyzer 12 and sample analyzer 112 that are common. In accordance with the embodiment illustrated in FIG. 2, the sample analyzer 112 has a detection unit 18 for analyzing the sample contained in a sample holder 42, a hemolyzer 60, a fluid handling unit 130, an optional sensor module 165, and a computing device 20 that controls operation of various components of the sample analyzer 112. The computing device 20 is in electronic communication with the detection unit 18, the fluid handling unit 130, and the sensor module 165 (when present) the hemolyzer 160.

Continuing with FIG. 2, the fluid handling unit 130 includes a bidirectional pump 135, an optional sensors module 165 for measuring co-oximetry analytes, multiple conduits 138a-138d for routing fluid sample between sensor module 165, the sample holder 42, the hemolyzer 60, and/or to waste storage 36. The sensor module 165 may include metabolite, electrolyte, and gas analyte sensors. The fluid handling unit 130 also includes a sample input valve 182, and another valve 184 to direct air 188 or fluids 186 into system. In certain cases, the fluid handling unit may be flushed with air and/or washed with fluid between tests.

The bidirectional pump 135, disposed at the end of fluidic path near the waste 36, pulls the sample S through the sensor module 165, into the sample vessel 42, and into the hemolyzer 60. The bidirectional pump 135 can then push the sample back into the sample vessel 42, and the hemolyzed blood sample is measured. Accordingly, the bidirectional pump 135 may be a peristaltic pump that can cause fluid sample to flow in both directions between the sample holder 42 and hemolyzer 60, and to waste storage 36 as needed. Conduit 138a couples the input valve 182 to the sensor module 165, conduit 138b couples to the sensor module 165 to the input side of the sample holder 42. Conduit 138c couples the sample holder 42 to the hemolyzer 60. Conduit 138d couples the hemolyzer 60 to the bidirectional pump 135 and to waste storage 36.

Continuing with FIG. 2, as discussed above, in operation the whole blood S may be optionally pulled into the sensor module 165 for co-oximetry tests, for example. The whole blood sample S may be directed to the sample holder 42, via the pump 135, where a first light absorbance profiled is obtained. The pump 135 can then cause the whole blood sample S to flow to the hemolyzer 60, where the whole blood sample is hemolyzed. The pump 135 can the cause the hemolyzed sample of blood to flow back to the sample holder 42, where the second absorbance profile is obtained. Once that is complete, the pump 135 can cause the hemolyzed sample to flow to waste storage 36. In some cases, air/water may be used to flush the sample holder and a further calibration may be performed. The analytical tools used to determine hemolysis levels are utilized as further described elsewhere.

The sample analyzers 12, 112 illustrated in FIGS. 1A, 1B, and 2 are exemplary sample analyzers that illustrate inventive concepts set forth in the present disclosure. The sample analyzers 12, 112 as described herein can be any type of sample analyzer adapted to make measurements of the sample using optical techniques, in particular, optical measurements of a whole blood sample. It should also be appreciated that the sample analyzer can be adapted to analyze multiple samples. In one example, the sample analyzer may be an automated analyzer that includes a moveable carousel for holding multiple sample vessels. Such an analyzer may include multiple detection units testing for different analytes of interest. An exemplary automated analyzer is disclosed in U.S. Patent App. Pub. No. 2010/0150779, incorporated herein by reference. Other exemplary sample analyzers include the ADVIA® and DIMENSION® analyzers marketed by Siemens Healthcare Diagnostics Inc.

Figure 3A:
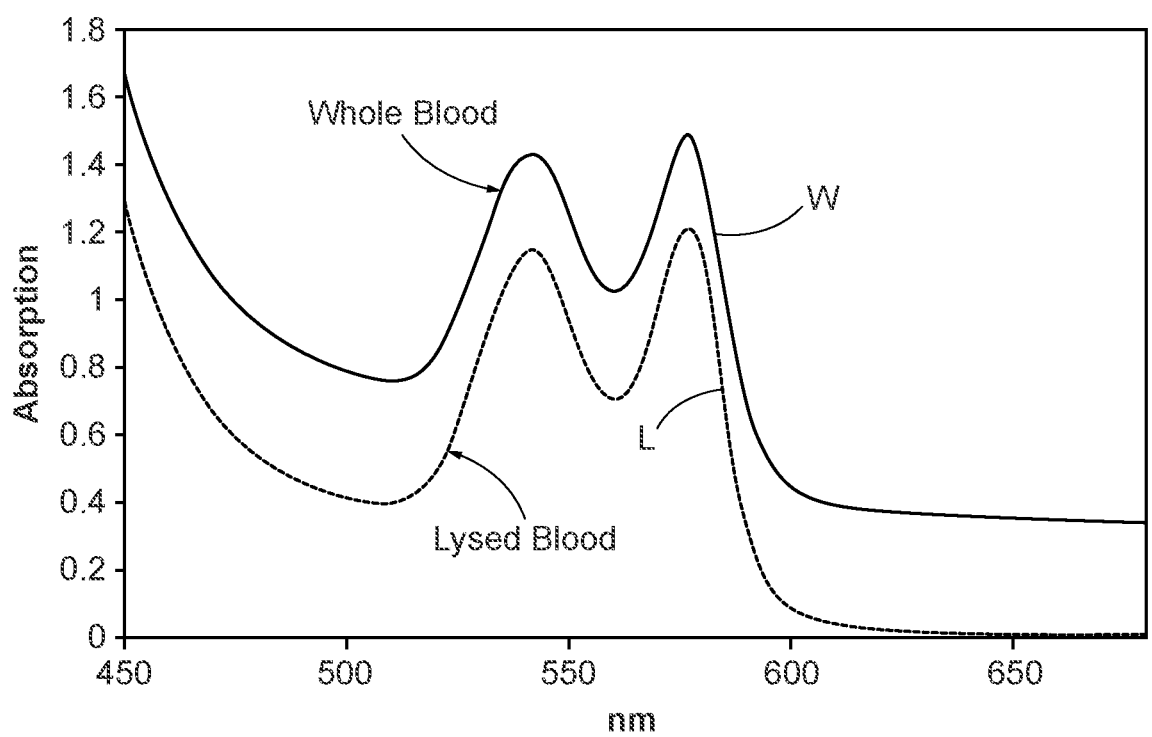
FIGS. 3A, 3B, and 3C illustrate exemplary absorbance spectra for whole blood samples.
Figure 3B:
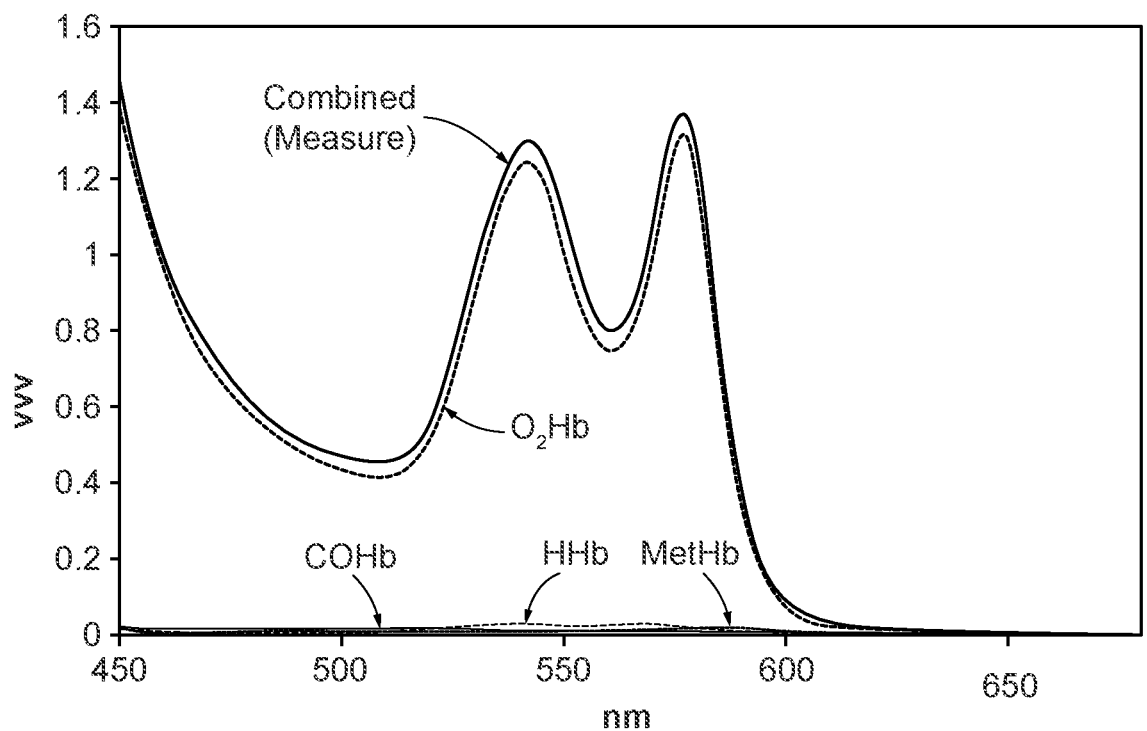
Figure 3C:
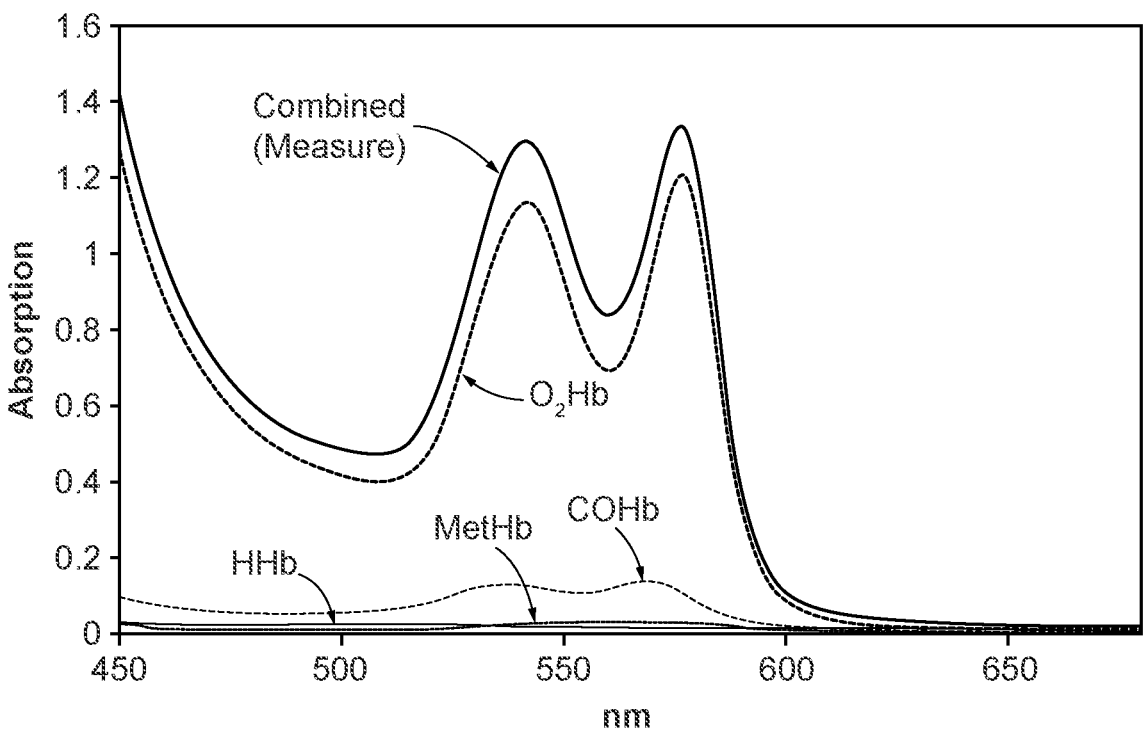
Figure 4A:
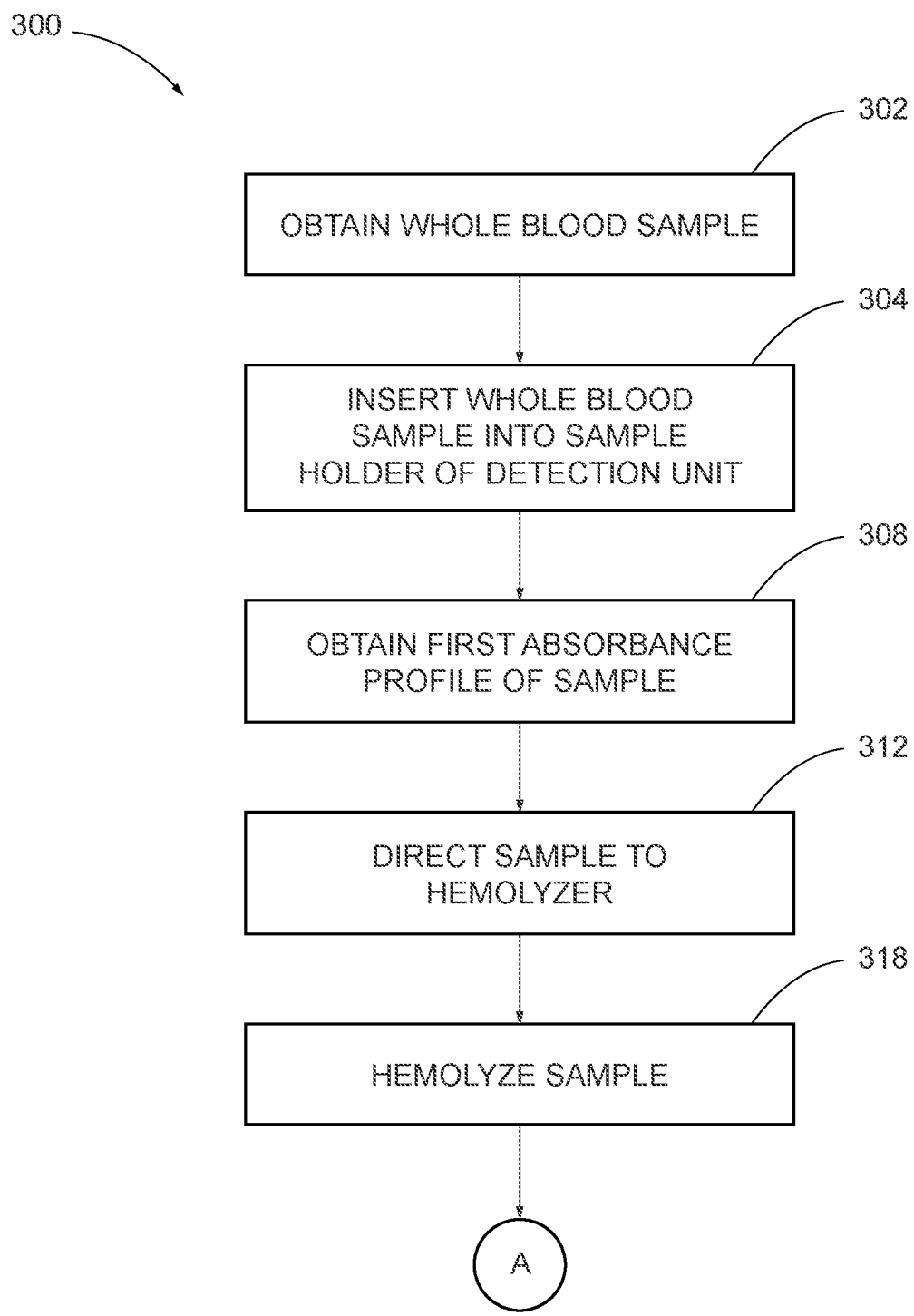
FIGS. 4A and 4B illustrate an exemplary process flow diagram for analyzing a whole blood sample according to an embodiment of the present disclosure.
Figure 4B:
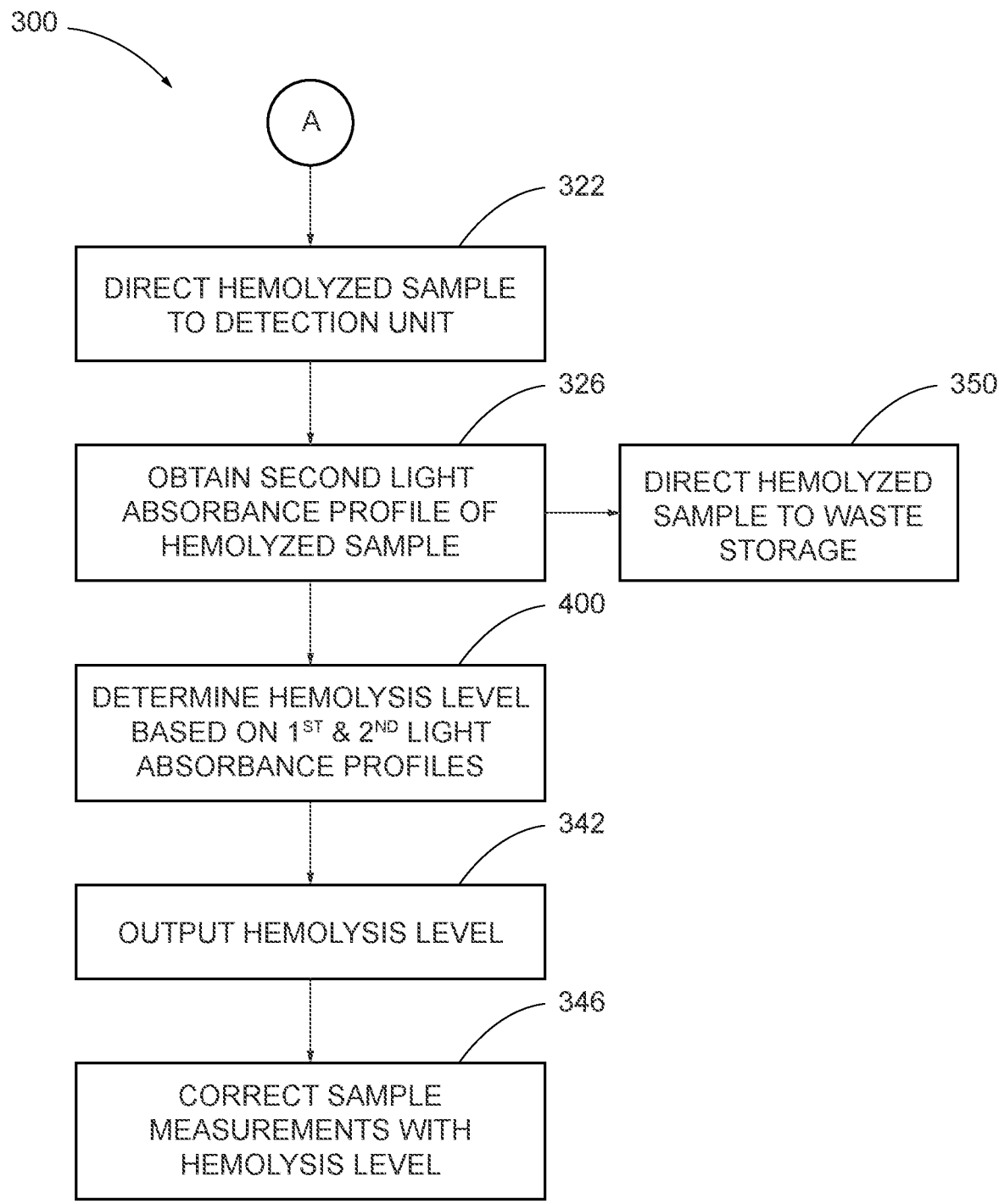
Figure 5:
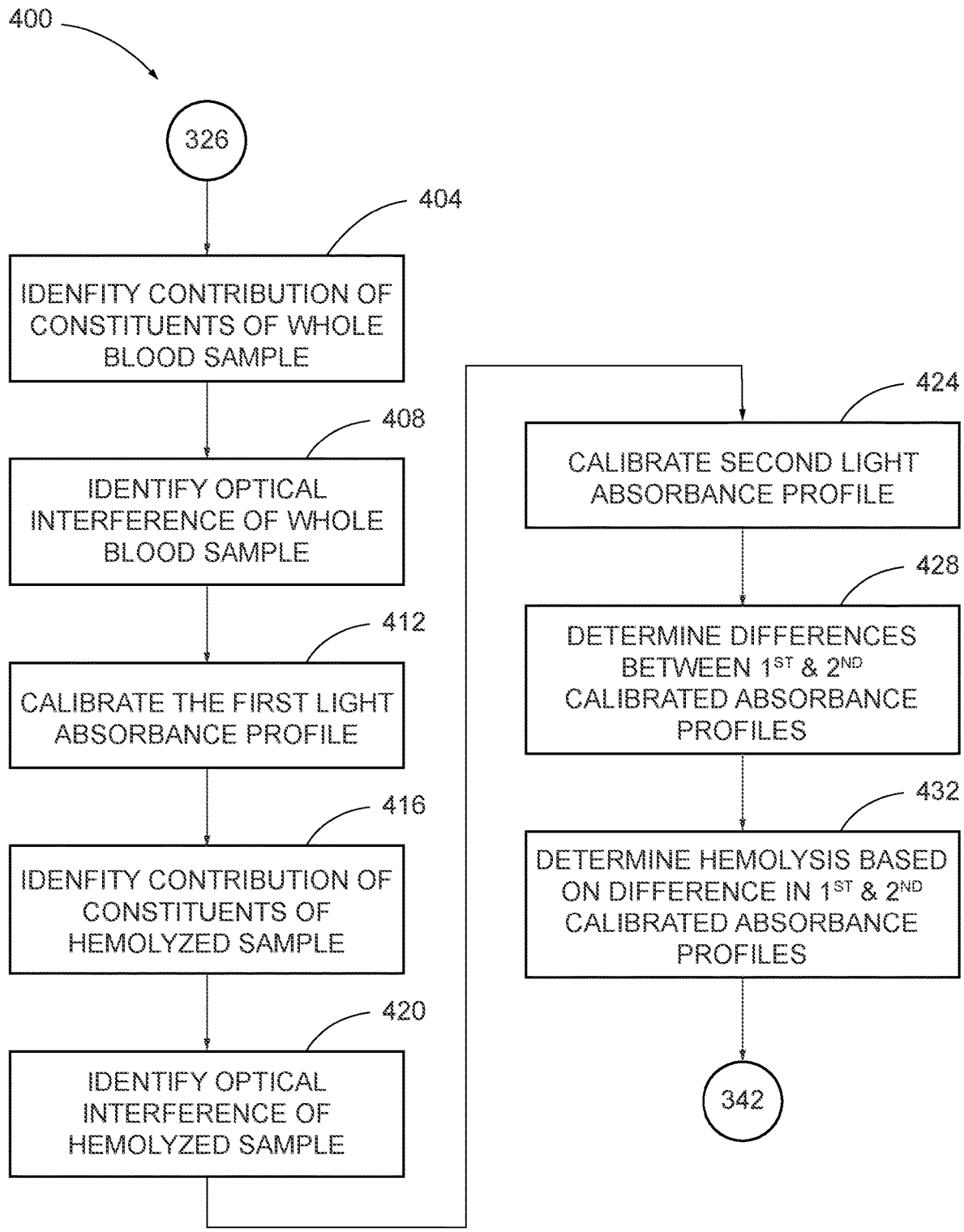
FIG. 5 is an exemplary method for determining a level of hemolysis in a whole blood sample based on absorbance spectra obtain before and after hemolyzing the whole blood sample in the method illustrated in FIGS. 4A and 4B.

FIGS. 3-5 illustrate general techniques for optical analysis of blood samples using the sample analyzer 12 and/or 112. Referring to FIG. 3A, the curve labeled 'whole blood' represents a combined absorbance spectrum W for a whole blood sample S obtained with the sample analyzer 12, 112. The illustrated absorbance spectrum W of the whole blood sample is referred to herein as the first light absorbance profile. The whole blood sample S is then intentionally, fully hemolyzed with hemolyzer 60 and a second light absorbance profile L is obtained (e.g., the curve labeled 'lysed blood'), which mirrors the 'whole blood' absorbance profile. By comparing the first and second light absorbance profiles W and L, the level of hemolysis in the whole blood sample S can be quantified. FIGS. 3B and 3C illustrate absorbance spectra for a whole blood sample that illustrates the absorbance measurements for variants of hemoglobin. The absorbance measurements for constituents of the whole blood before and after full hemolysis represent the concentrations of the illustrated constituents in the blood sample. Blood constituents as used herein include, but are not limited, to hemoglobin and its variants, such as total hemoglobin (tHb), oxygen saturation of hemoglobin ($sO_2$), oxyhemoglobin ($O_2Hb$), deoxygenated hemoglobin (HHb), methemoglobin (MetHb) and total bilirubin.

FIGS. 4A, 4B, and 5 illustrate one exemplary method 300 for analyzing a blood sample. The method 300 includes optical determination of level of hemolysis of a whole blood sample in accordance with the inventive concepts described herein. Referring to FIG. 4A, in step 302, a whole blood sample S is obtained from the patient. Techniques for obtaining the whole blood sample are typical and are known to persons of skill in the art. Typically, however, the whole blood sample is extracted from the patient with a syringe, needle or indwelling port and the blood sample is pulled into a sample tube or vial. For instance, the whole blood sample can be an arterial or venous whole blood sample. Arterial samples are obtained with a syringe which is placed directly on the instrument. Venous samples are drawn into a vacuum tube from a needle or an indwelling shunt. The whole blood sample is introduced to the sample analyzer 12, 112. In particular, in step 304, the whole blood sample S is inserted into sample holder 42 of the detection unit 18. A sample vial may be inserted directly into the sample holder 42. Alternatively, the sample vial is used to feed the whole blood sample to a dispensing unit that, in turn, dispenses the whole blood sample S to the sample holder 42. In still another alternative, the sample vial is placed in a cartridge and the cartridge is inserted into the sample analyzer 12, 112 and interfaces with the dispensing unit. In such an embodiment, the dispensing unit delivers the whole blood sample to the sample holder 42.

As shown in FIG. 4A, in step 308, the detection unit 18 obtains a first light absorbance profile W of the whole blood sample S. Obtaining the first light absorbance profile W includes emitting a first light signal from the illuminator 40 into the whole blood sample S contained in the sample holder 42. In one example, the sample holder 42 provides a path length of 0.05-0.5 mm. The first light signal may be a full spectrum signal. The detector 44 measures the light signal that is not absorbed by the whole blood sample S to obtain absorbance measurements for range of wavelengths, which is compiled into the first light absorbance profile W. An exemplary first light absorbance profile W is shown in FIG. 3A. In one example, the first light absorbance profile W includes absorbance measurements for up to 50 or more wavelengths. In another example, the first light absorbance profile W includes absorbance measurements for up to 128 or more wavelengths. In another example, the first light absorbance profile W includes absorbance measurements for up to 250 or more wavelengths. The detection unit 18 transmits data indicative of the first light absorbance profile W to the computing device 20. The first light absorbance profile W may be stored in the memory 24 of the computing device 20.

Continuing with FIG. 4A, after obtaining the first light absorbance profile W from the whole blood sample S, the sample is directed to the hemolyzer 60 in step 312. In step 312, the computing device 20 sends a control signal to the valve 34 to direct fluid from the sample holder 42 to the hemolyzer 60 via conduits 38c and 38d. In step 318, the hemolyzer 60 intentionally hemolyzes the whole blood sample S. As discussed above, the whole blood sample S may be mechanically hemolyzed. Alternatively and/or additionally, the whole blood sample may be chemically hemolyzed to cause the cell wall to rupture. The computing device 20 can send control signals to the hemolyzer 60 to direct intentional hemolysis of the whole blood sample.

Turning to FIG. 4B, in step 322, the hemolyzed sample is directed from the hemolyzer 60 to the sample holder 42 of the detection unit 18. In particular, the computing device 20 sends a control signal to the hemolyzer to direct the sample fluid to the valve 32 via conduit 38b. The computing device 20 also sends a control signal to the valve 32 to direct the sample fluid to the sample holder 42 through conduit 38a.

As shown in FIG. 4B, in step 326, the detection unit 18 obtains a second light absorbance profile L of the hemolyzed whole blood sample. Obtaining the second light absorbance profile L includes emitting a second light signal from the illuminator 40 into the hemolyzed blood sample. The detector 44 measures the second light signal that is not absorbed by the hemolyzed blood sample to develop the second light absorbance profile L. An exemplary second light absorbance profile is shown in FIG. 3A. In one example, the second light absorbance profile L includes absorbance measurements for up to 50 or more wavelengths. In another example, the second light absorbance profile L includes absorbance measurements for up to 128 or more wavelengths. In another example, the second light absorbance profile L includes absorbance measurements for up to 250 or more wavelengths. In another example, the second light absorbance profile L may include full spectrum absorbance measurements. The detection unit 18 transmits data indicative of the second light absorbance profile L to the computing device 20. The second light absorbance profile L may be stored in the memory 24 of the computing device 20. After step 326, the hemolyzed sample is routed by valve 34 to waste storage 36 via conduit 38e.

As shown in FIG. 5, the level of hemolysis in the whole blood sample is determined in step 400. In step 400, two basic operations are implemented. First, the first light absorbance profile W and the second light absorbance profile L are analyzed. Second, in response to the analysis of the first light absorbance profile W and the second light absorbance profile L, the level of hemolysis in the whole blood sample S is determined. In general, the level of hemolysis of the whole blood sample is determined based on the difference between contribution of constituents of whole blood to absorbance spectrum before and after hemolyzing the sample. The constituents of whole blood may include, but are not limited to, plasma, and/or serum, red blood cells, white blood cells, and variants of hemoglobin contained in the red blood cells. Other constituents of blood may include tHb, $sO_2$, $O_2Hb$, HHb, MetHb, turbidity, and total bilirubin. The "contribution of constituents of whole blood" to the absorbance spectrum refers to a relative measure the absorbance measurement of one component of the blood sample to the overall absorbance spectrum. In particular, some hemoglobin variants may dominate the absorbance spectrum rendering the absorbance measurements for other hemoglobin components appear insignificant. The methods described herein account for relative weight one component has over the others absorbance data. Determining the level of hemolysis in the whole blood sample in step 400 may be accomplished by a variety of different several analytical methods. Regardless of which specific analytical technique to determine hemolysis is used, after step 400, optional data corrections and/or output steps may occur and will be described in more detail below.

One embodiment for analyzing the first and second light absorbance profiles to determine the hemolysis level in a whole blood sample S is shown in FIG. 5 as method 400. Method 400 includes additional sub operations executed by the computer processor that analyze the absorbance data in order to determine the hemolysis level. Method 400 initiates with step 404. In step 404, a computer processor 22 identifies a first contribution of constituents of the whole blood sample to the first light absorbance profile. In one example, the constituents of the whole blood sample are variants of hemoglobin, such as tHb, $sO_2$, $O_2Hb$, HHb, MetHb, and total bilirubin. Identifying the contribution of the blood constituents to the first light absorbance profile may be based on clinical data stored in computing device 20. The clinical data may be obtained from a statistically significant number of samples obtained from a patient population and an analysis of the absorbance spectra of those samples. Various analytical tools familiar to a person of skill in the art may be implemented as software instructions executed by a computer processor in order to identify the contribution of the constituents of the whole blood sample to the first light absorbance profile W.

In step 408, the computer processor 22 identifies any possible optical interference in the whole blood sample. Optical interferences may include changes in path length of the first light signal through the whole blood sample, scatter effects, and/or non-absorbance of the first light signal through the whole blood sample. The path length in the sample measurement vessel in theory is constant. However the measurement vessel path in practice becomes compromised, decreased, over time due to a buildup residue from many blood samples tested (e.g. proteins) not completely removed by the wash cycle. A calibration process not described herein may performed periodically and during this the actual path length is may be measured using a quality control standard dye solution, as is known to those skilled in the art.

In step 412, the computer processor corrects the first light absorbance profile based on 1) the first contribution of the constituents identified in step 404, and 2) the optical interferences identified in step 408. Correcting the first light absorbance profile in step 412 may include additional sub operations executed by the computer processor. In one example, the first light absorbance profile is corrected by taking into account optical interferences in the whole blood sample. For example, if the first light signal is refracted and altered in some manner, such as when there is protein build on the vessel wall as described above, and the path length is longer (or shorter), than the designed path length of the sample holder 42, the absorbance spectrum of the whole blood sample may be altered or inaccurate. Step 412 may include a sub operation for determining an effect of path length of the first light signal through the whole blood sample. In addition, certain cellular structures, blood constituents, or vessel surfaces cause scatter that alters the absorbance spectrum. Step 412 may also include a determination of the effect of scatter of the first light signal through the whole blood sample. In some instances, components of the light signal are not being absorbed by the whole blood sample at all. Step 412 may also include determining an effect of non-absorbance of the first light signal by the whole blood sample. Optical interference effects may be compiled as reference vectors of a spectrum and used as a reference and/or as a correction technique to account for effect of optical interferences in the whole blood sample on the first light absorbance profile. The computer processor 22 corrects the first light absorbance profile once the effects of optical interference are determined. Accordingly, the corrected first light absorbance profile may be based on 1) the first contribution of the blood constituents, and 2) the determined effect of a) path length, b) scatter, and/or c) the non-absorbance of the first light signal.

Correcting the first and second light absorbance profiles may be accomplished according to the methods and techniques described in U.S. Pat. No. 6,172,744 (the 744 patent). The entire disclosure of the 744 patent is incorporated by reference into the present application. In one embodiment, absorbance differences between the first and second light absorbance profiles may be compared by, for example, comparing each individual blood constituent to reference spectra vectors of whole blood, partially hemolyzed, and/or fully hemolyzed blood as described in the 744 patent.

Step 416 includes identifying via the computer processor 22 a second contribution of constituents of the hemolyzed blood sample to the second light absorbance profile. Identifying the contribution of blood constituents of the hemolyzed blood sample to the second light absorbance profile may be based on clinical data obtained from a statistically significant number samples obtained from a patient population and an analysis of the absorbance spectra of those sample types. In accordance with this example, the computer processor 22 identifies the constituents of the hemolyzed blood sample using typical analytical techniques.

Step 420 includes identifying optical interferences in the second light absorbance profile related to the hemolyzed blood sample. The optical interferences for the hemolyzed sample are similar to the optical interferences for whole blood sample, and include a) path length of the second light signal, b) scatter of the second light signal, and c) non-absorbance of components of the second light signal.

In step 424, the computer processor 22 corrects the second light absorbance profile based on 1) the contribution of constituents of the hemolyzed sample identified in step 416, and 2) the optical interferences identified in step 420. Correcting the second light absorbance profile may include additional (optional) sub operations that are similar to the sub operations used to correct the first light absorbance profiled in step 412 described above. For instance, step 424 may include an optional step determining an effect of path length of the second light signal through the hemolyzed blood sample. In addition, the step 424 may optionally include determining an effect of scatter of the second light signal through the hemolyzed blood sample. Step 424 may also include determining an effect of non-absorbance of the second light signal by the constituents of the hemolyzed blood sample. Then, the computer processor 22 corrects the second light absorbance profile after the effects of the optical interferences described above on the hemolyzed blood sample are determined. Thus, the corrected second light absorbance profile may be based on 1) the second contribution of blood constituents to the second absorbance profile, and 2) the determined effect of a) path length, b) scatter, and/or c) the non-absorbance of the second light signal. Determining the effects of the optical interference and correcting the spectra may be accomplished according to the methods and techniques described in the 744 patent. Process control is transferred to step 428

In step 428, the computer processor 22 determines differences between the corrected first light absorbance profile and the corrected second light absorbance profile. In step 432, the level of hemolysis in the whole blood sample is derived from the differences between the corrected first light absorbance profile and the corrected second light absorbance profile. One example of deriving the differences between the corrected spectra may be the methods described in 744 patent. At this point, the process control is transferred to step 342 (FIG. 4B) and the hemolysis level of the whole blood samples is output as needed.

Figure 9:
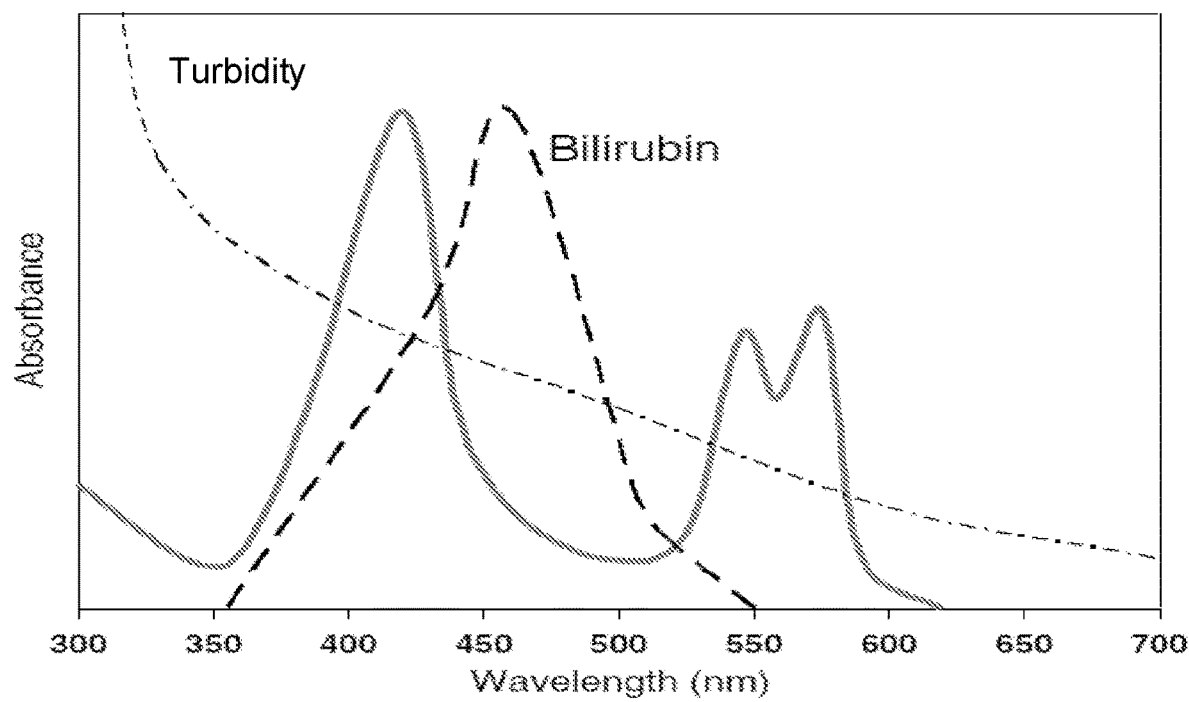
FIG. 9 illustrates the absorbance spectra of blood hemoglobin, blood turbidly, and blood bilirubin.

The methods described above may use light absorbance profiles to characterize interferences that are present in the original sample (e.g. whole blood with unknown hemolysis). These interferences may include: lipids, bilirubin and cell casing debris. Lipids and bilirubin are extracellular, the change in concentration from measurement to measurement typically remains constant. However, constituent concentrations vary from patient sample to patient sample, they also possess different lipids and bilirubin profiles, proportional to their individual blood profile. In most all cases they possess different levels of hemolysis proportional to the sample integrity. In other words, unless the patient has a very rare autoimmune disease, then the hemolysis is not proportional to their blood profile. Natural hemolysis occurs at very low levels which is consistent with RBC turnover which is ~120 days in healthy patients. Generally, lipids cause scatter across the entire spectrum. Bilirubin absorbs at wavelengths shorter than 520 nm. Understanding the contribution of the cell casing debris may be useful to evaluating hemolysis in the methods described herein. FIG. 9 illustrates an absorbance spectra of blood hemoglobin, blood turbidity, and blood bilirubin. Science Direct, Clinica Chimica Acta, *Harmonization of automated hemolysis index assessment and use: Is it possible?* Alberto Dolci, Mauro Panteghini. As can be seen in FIG. 9, the spectral signature of extracellular bilirubin is distinguishably different than the signature of lipids, especially in the range of 400 nm to 520 nm compared to 610 nm to 680 nm. Lipid molecules, which include triglycerides, cholesterol, apolipoproteins and chylomicrons, scatter shorter wavelength 450 nm light rays compared to longer wavelength 680 nm light rays. Cell casings suspended in the plasma after hemolysis have a unique signature, this signature is determined to a high degree of accuracy and precision, consequently this enables methods described herein to compensate for hemolyzed blood in a way that an accurate and precise. Thus, the scattering effect of constituents allows the spectral profiles for the constituents to be applied using the methods described herein to improve hemolysis result accuracy and measurements.

Figure 6:
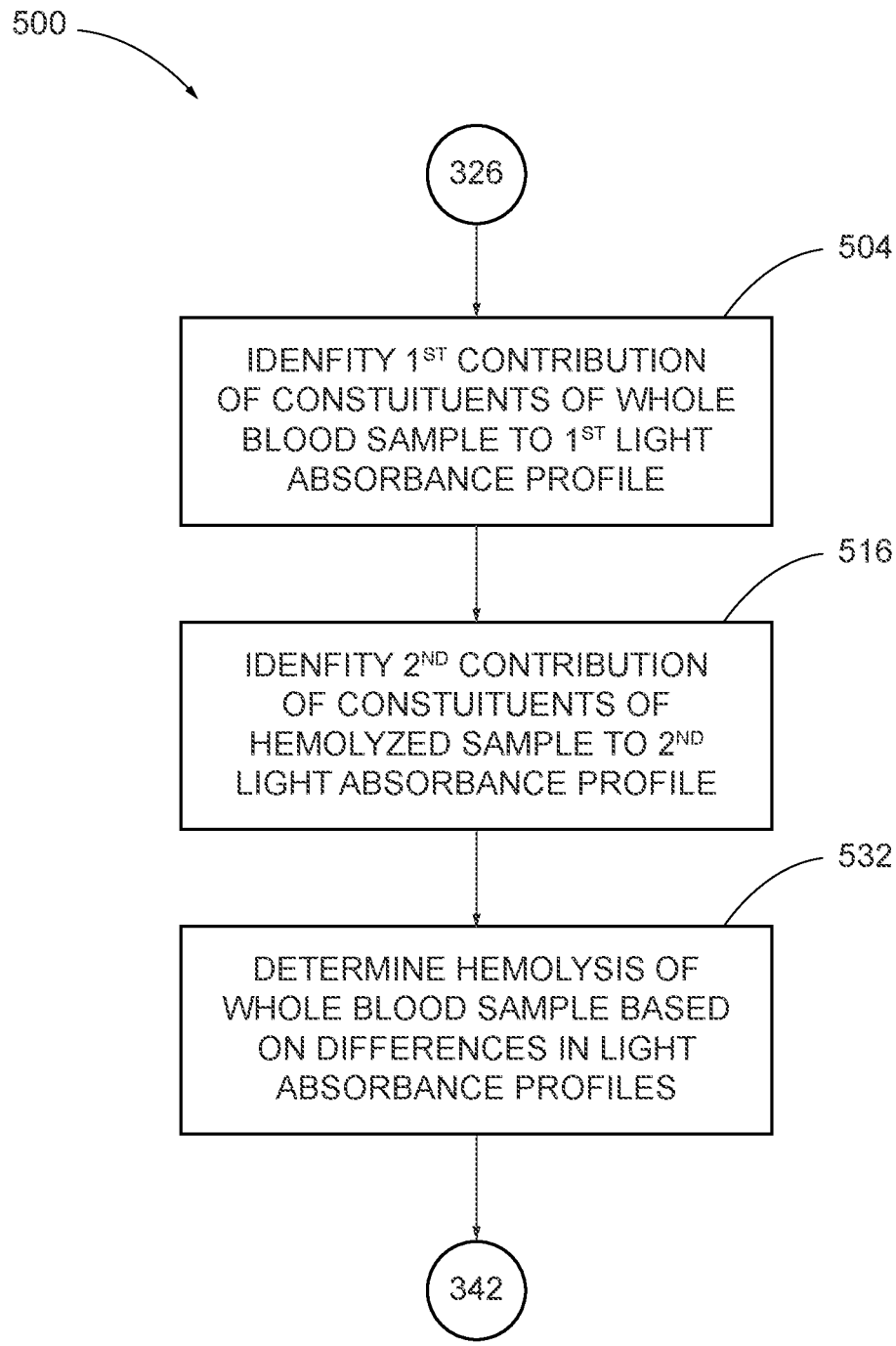
FIG. 6 is an alternative method for determining a level of hemolysis in a whole blood sample.
Figure 7:
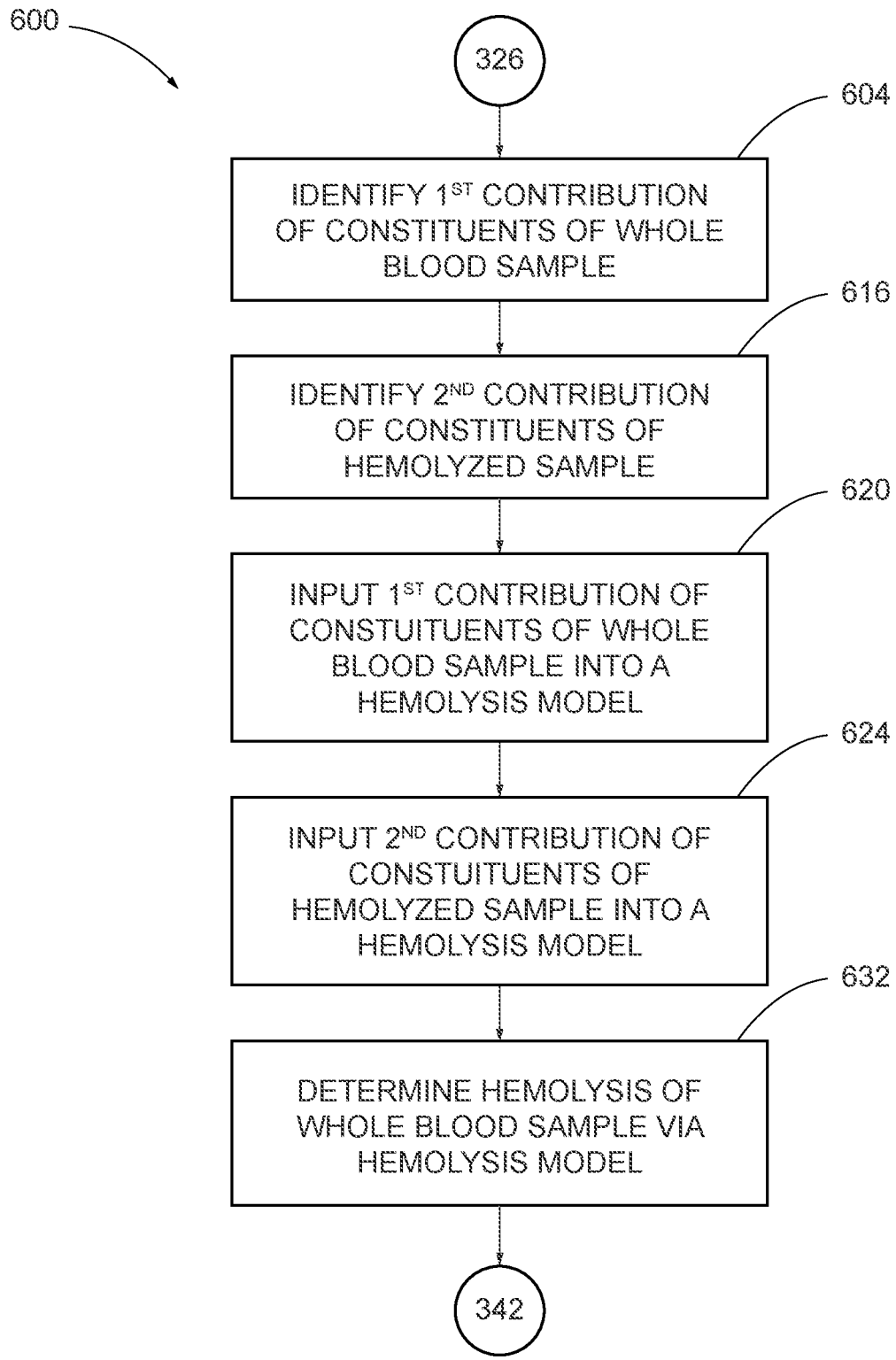
FIG. 7 is an alternative method for determining a level of hemolysis in a whole blood sample.

Several alternatives may be used to determine the hemolysis level based on analysis of light absorbance profiles before and after hemolyzing the whole blood sample. FIGS. 6 and 7 illustrate alternative analytical operations for determining the hemolysis level in the whole blood sample. Each analytical method described below method 500 (FIG. 6), method 600 (FIG. 7), and method 700 (FIG. 8) are performed in response to obtaining the second light absorbance profile of the hemolyzed sample in step 326 (FIG. 4B). The output of each method 500, 600, and 700 is to output the determined hemolysis level in step 342.

Referring to FIG. 6, the computer processor implements method 500 after the second light absorbance profile is obtained in step 326. In step 504, the computer processor 22 identifies the contribution of the constituents of the whole blood sample to the first light absorbance profile. Step 504 implements techniques to identify the contribution of constituents of the whole blood sample as described above. Identification of the contribution of the constituents of the blood may be based on clinical data stored in computing device 20. Step 516 includes identifying via the computer processor 22 a second contribution of the constituents of the hemolyzed blood sample to the second light absorbance profile. In step 532, the computer processor 22 determines the level of hemolysis based on the differences between: a) the first contribution of constituents of the whole blood sample to the first light absorbance profile, and b) the second contribution of constituents of the hemolyzed blood sample to the second light absorbance profile. The differences may be an offset between the first and second absorbance profiles for various constituents, differences in slope of various portions of the absorbance profiles, and/or other differences between the absorbance profiles that yield an acceptable threshold of clinical precision. Process control is transferred to step 342 (FIG. 4B).

FIG. 7 illustrates an alternative method 600 for determining the level of hemolysis in the whole blood sample. In step 604, the computer processor 22 identifies the contribution of the constituents of the whole blood sample to the first light absorbance profile. Step 616 may include identifying via the computer processor 22 a second contribution of the constituents of the hemolyzed blood sample to the second light absorbance profile. Method 600 includes use of a hemolysis model to determine hemolysis level of whole blood. The hemolysis model may be a set relationship among known inputs for a whole blood sample based on clinical data stored in computing device 20. The clinical data may be obtained from a statistically significant number of samples obtained from a patient population and measured hemolysis levels based on absorbance spectra of those samples. The hemolysis model may provide outputs that are indicative of hemolysis level in the whole blood sample based on the inputs into the model. In step 620, the computer processor 22 inputs into the hemolysis model the contribution of constituents of the whole blood sample to the first light absorbance profile. In step 624, the computer processor 22 inputs into the hemolysis model the contribution of the constituents of the hemolyzed blood sample to the second light absorbance profile. In step 632, the computer processor determines the level of hemolysis of the whole blood sample based on the hemolysis model.

Figure 8:
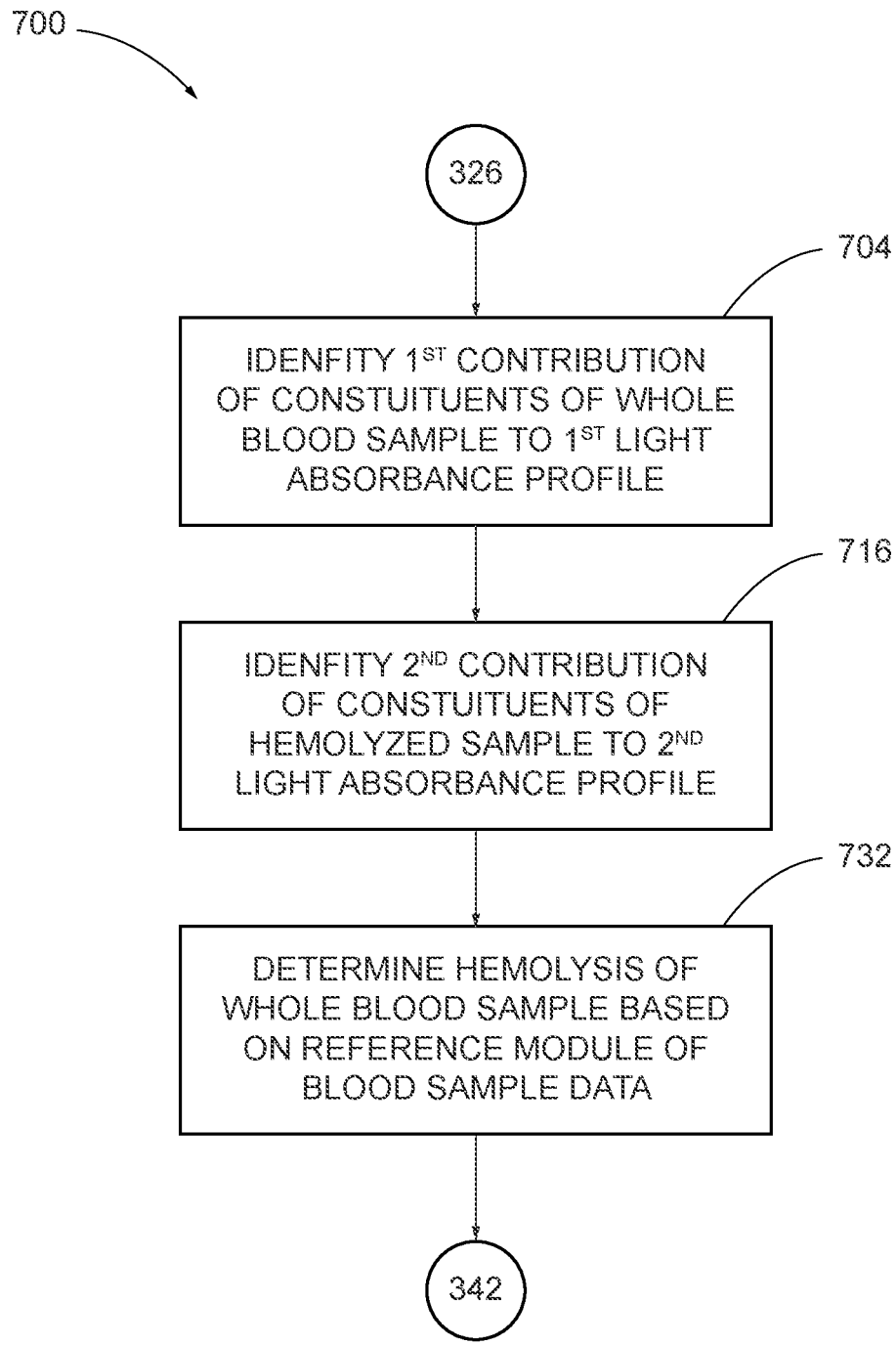
FIG. 8 is an alternative method for determining a level of hemolysis in a whole blood sample.

Another alternative to determining hemolysis is illustrated in FIG. 8. In FIG. 8, method 700 determines the level of hemolysis in the whole blood sample based on reference module. In step 704, the computer processor 22 identifies the contribution of the constituents of the whole blood sample to the first light absorbance profile. Step 716 includes identifying via the computer processor 22 a second contribution of the constituents of the hemolyzed blood sample to the second light absorbance profile. In step 732, the computer processor 22 compares the first and second contributions of the blood constituents to a reference module. The reference module may be a database that correlates hemolysis levels of whole blood to the relative contributions of the constituents of the whole blood sample and the relative contributions of constituents of the hemolyzed blood sample. For instance, given a known absorbance profile for the whole blood sample (and the hemolyzed sample), a level of hemolysis can be retrieved that corresponds to the measured data. The reference module can likewise operate as a look-up table. Given known contributions of constituents of blood to absorbance profiles, the level of hemolysis levels may be determined with reference to the look-up table. Process control is transferred to step 342.

Referring to back to FIG. 4B, once the level of hemolysis is determined in step 400 (or alternatively in method 500, 600, 700), the computing device 20 outputs the hemolysis level in step 342.

Continuing with FIG. 4B, method 400 may include correction of other measurements from the whole blood sample based on the determined hemolysis level. Step 346 includes obtaining a measurement of an analyte of the whole blood sample and correcting the measurement of the analyte based on the determined level of hemolysis in the whole blood sample. Step 346 may be applied to either a blood assay or an assay of plasma and/or serum. In one example, the method includes obtaining a measurement of an analyte in the whole blood sample in a blood assay and correcting the measurement of the analyte based on the determined level of hemolysis in the whole blood sample. In another example, step 346 may include obtaining plasma or serum from the whole blood sample. The method 400 may include obtaining a measurement of an analyte from the plasma or serum and then correcting the measurement of the analyte based on the determined level of hemolysis in the whole blood sample.

The inventive concepts further include the following listed embodiments.

1. A method, comprising:
 obtaining a whole blood sample;
 obtaining a first light absorbance profile of the whole blood sample;
 hemolyzing the whole blood sample to generate a hemolyzed sample of blood;
 obtaining a second light absorbance profile of the hemolyzed sample of blood; and
 determining a level of hemolysis in the whole blood sample by comparing the first light absorbance profile and the second light absorbance profile.

2. The method of embodiment 1, further comprising:
 placing the whole blood sample in a sample holder of a sample analyzer;
 directing the whole blood sample to a hemolyzer before hemolyzing the whole blood sample; and
 after hemolyzing the whole blood sample, directing the hemolyzed sample of blood to the sample holder in the sample analyzer.

3. The method of embodiment 1, wherein obtaining the first light absorbance profile includes directing a first light signal into the whole blood sample, and wherein obtaining the second light absorbance profile includes directing a second light signal into the hemolyzed sample of blood.

4. The method of embodiment 1, wherein determining the level of hemolysis in the whole blood sample includes:
 identifying a first contribution of constituents of the whole blood sample to the first light absorbance profile;
 identifying a second contribution of constituents of the hemolyzed blood sample to the second light absorbance profile; and
 determining the level of hemolysis based on the difference between 1) the first contribution of constituents of the whole blood sample to the first light absorbance profile, and 2) the second contribution of constituents of the hemolyzed blood sample to the second light absorbance profile.

5. The method of embodiment 1, wherein determining the level of hemolysis in the whole blood sample includes:
 identifying a first contribution of constituents of the whole blood sample to the first light absorbance profile;
 identifying at least one optical interference of the whole blood sample; and
 correcting the first light absorbance profile based on 1) the first contribution of constituents of the whole blood sample, and 2) the at least one optical interference of the whole blood sample.

6. The method of embodiment 5, wherein determining the level of hemolysis in the whole blood sample includes: determining a difference between the corrected first light absorbance profile and the second light absorbance profile to obtain the level of hemolysis in the whole blood sample.

7. The method of embodiment 5, wherein determining the level of hemolysis in the whole blood sample further includes:
 identifying a second contribution of constituents of the hemolyzed blood sample to the second light absorbance profile;
 identifying at least one optical interference in the second light absorbance profile of the hemolyzed blood sample; and
 correcting the second light absorbance profile based on 1) the second contribution of the constituents of the hemolyzed blood sample, and 2) the at least one optical interference of the hemolyzed blood sample.

8. The method of embodiment 7, wherein determining the level of hemolysis in the whole blood sample further includes:

determining a difference between the corrected first light absorbance profile and the corrected second light absorbance profile to obtain the level of hemolysis in the whole blood sample.

9. The method of embodiment 7, wherein the at least one optical interference is a path length of a first light signal through the whole blood sample, a scatter of the first light signal through the whole blood sample, and non-absorbance of the first light signal by the whole blood sample, wherein correcting the first light absorbance profile is based on a) the first contribution of the constituents to the whole blood sample, b) an effect of the path length of the first light signal through the whole blood sample, c) an effect of the scatter of the first light signal through the whole blood sample, and d) an effect of the non-absorbance of the first light signal by the whole blood sample.

10. The method of embodiment 9, wherein the at least one optical interference is a path length of a second light signal through the hemolyzed blood sample, a scatter of the second light signal through the hemolyzed blood sample, and non-absorbance of the second light signal by the hemolyzed blood sample, wherein correcting the second light absorbance profile is based on a) the second contribution of the constituents of the blood sample, b) an effect of the path length of the a second light signal through the hemolyzed blood sample, c) an effect of the scatter of the second light signal through the hemolyzed blood sample, and d) an effect of the non-absorbance of the second light signal by the hemolyzed blood sample.

11. The method of embodiment 1, wherein determining the level of hemolysis in the whole blood sample includes:

identifying a first contribution of constituents of the whole blood sample to the first light absorbance profile;

identifying a second contribution of constituents of the hemolyzed blood sample to the second light absorbance profile;

quantifying the level of hemolysis in the whole blood sample via a hemolysis model, wherein the hemolysis model outputs the level of hemolysis based on a) the first contribution of constituents of the whole blood sample to the first light absorbance profile, and b) the second contribution of constituents of the hemolyzed blood sample to the second light absorbance profile.

12. The method of embodiment 1, wherein determining the level of hemolysis in the whole blood sample includes:

identifying a first contribution of constituents of the whole blood sample to the first light absorbance profile;

identifying a second contribution of constituents of the hemolyzed blood sample to the second light absorbance profile; and determining the level of hemolysis in the whole blood sample based on a reference module of hemolysis levels of whole blood that correspond to first and second contributions of constituents of blood to the first and second absorbance profiles, respectively.

13. The method of embodiment 1, further comprising:

obtaining a measurement of an analyte of the whole blood sample; and correcting the measurement of the analyte based on the determined level of hemolysis in the whole blood sample.

14. The method of embodiment 1, further comprising:

obtaining plasma or serum from the whole blood sample;

obtaining a measurement of an analyte from the plasma or serum; and correcting the measurement of the analyte based on the determined level of hemolysis in the whole blood sample.

15. The method of embodiment 1, wherein directing the whole blood sample to the hemolyzer includes routing the whole blood sample directly from the sample holder to the hemolyzer.

16. The method of embodiment 1, wherein directing the hemolyzed sample of blood to sample holder includes routing the hemolyzed sample of blood directly from the hemolyzer to the sample holder.

17. The method of embodiment 1, wherein the method further comprises, after obtaining the second light absorbance profile, directing the hemolyzed sample of blood from the sample holder to waste storage.

18. The method of embodiment 1, further comprising directing the flow of sample between the sample holder and the hemolyzer with a bidirectional pump.

19. A system for analyzing components of whole blood, the system comprising:

a detection unit for obtaining a first light absorbance profile of a whole blood sample and a second light absorbance profile of a hemolyzed sample of blood;

a hemolyzer for hemolyzing the whole blood sample into the hemolyzed sample of blood; and a computer processor in communication with the detection unit, the computer processor configured to execute instructions that determine a level of hemolysis of the whole blood by comparing the first light absorbance profile of the whole blood sample to the second light absorbance profile of the hemolyzed sample.

20. The system of embodiment 19, further comprising:

a sample holder; and a fluid handling unit including a plurality of valves, the valves configured to direct the whole blood sample from the sample holder to the hemolyzer and to the direct the hemolyzed sample of blood to the sample holder 21. The system of embodiment 19, wherein the computer processor executes instructions that:

identify a first contribution of constituents of the whole blood sample to the first light absorbance profile;

identify a second contribution of constituents of the hemolyzed blood sample to the second light absorbance profile; and determine the level of hemolysis based on a difference between 1) the first contribution of constituents of the whole blood sample to the first light absorbance profile, and 2) the second contribution of constituents of the hemolyzed blood sample to the second light absorbance profile.

22. The system of embodiment 19, wherein the computer processor executes instructions that:

identify a first contribution of constituents of the whole blood sample to the first light absorbance profile;

identify at least one optical interference in the first light absorbance profile of the whole blood sample; and correct the first light absorbance profile based on 1) the first contribution of the constituents of the whole blood sample to the first light absorbance profile, and 2) the at least one optical interference of the whole blood sample.

23. The system of embodiment 22, wherein the computer processor executes instructions that: determine a difference between the corrected first light absorbance profile and the second light absorbance profile to obtain the level of hemolysis in the whole blood sample.

23. The system of embodiment 22, wherein the computer processor executes instructions that:

identify a second contribution of constituents of the hemolyzed blood sample to the second light absorbance profile;

identify at least one optical interference in the second light absorbance profile of the hemolyzed blood sample; and correct the second light absorbance profile based on 1) the second contribution of the constituents of the hemolyzed blood sample, and 2) the at least one optical interference of the hemolyzed blood sample.

24. The system of embodiment 23, wherein the computer processor executes instructions that: determine a difference between the corrected first light absorbance profile and the corrected second light absorbance profile to obtain the level of hemolysis in the whole blood sample.

25. The system of embodiment 23, wherein the at least one optical interference is a path length of a first light signal through the whole blood sample, scatter of the first light signal through the whole blood sample, and non-absorbance of the first light signal by the whole blood sample, wherein the computer processor executes instructions that:

correct the first light absorbance profile is based on a) the first contribution of the constituents to the whole blood sample, b) an effect of the path length of the first light signal through the whole blood sample, c) an of the effect the scatter of the first light signal through the whole blood sample, and d) an effect of the non-absorbance of the first light signal by the whole blood sample.

26. The system of embodiment 25, wherein the at least one optical interference is a path length of a second light signal through the hemolyzed blood sample, scatter of the second light signal through the hemolyzed blood sample; and non-absorbance of the second light signal by the hemolyzed blood sample, wherein the computer processor executes instructions that:

correct the second light absorbance profile is based on a) the second contribution of the constituents of the hemolyzed blood sample, b) an effect of the path length of the a second light signal through the hemolyzed blood sample, c) an effect of the scatter of the second light signal through the hemolyzed blood sample, and d) an effect of the non-absorbance of the second light signal by the hemolyzed blood sample.

27. The system of embodiment 22, wherein the computer processor is configured to execute instructions that:

identify a first contribution of constituents of the whole blood sample to the first light absorbance profile;

identify a second contribution of constituents of the hemolyzed blood sample to the second light absorbance profile;

determine the level of hemolysis in the whole blood sample with a hemolysis model based on a) the first contribution of constituents of the whole blood sample to the first light absorbance profile, and b) the second contribution of constituents of the hemolyzed blood sample to the second light absorbance profile.

28. The system of embodiment 22, wherein the computer processor is configured to execute instructions that:

identify a first contribution of constituents of the whole blood sample to the first light absorbance profile;

identify a second contribution of constituents of the hemolyzed blood sample to the second light absorbance profile; and determine the level of hemolysis in the whole blood sample based on a reference module of hemolysis levels of whole blood that correspond to first and second contributions of constituents of the blood to the first and second absorbance profiles, respectively.

29. The system of embodiment 22, wherein the computer processor executes instructions that: correct a measurement of an analyte of the whole blood sample obtained from the whole blood sample based on the determined level of hemolysis in the whole blood sample.

30. The system of embodiment 20, wherein the computer processor executes instructions that: correct a measurement of an analyte from plasma or serum obtained from the whole blood sample based on the determined level of hemolysis in the whole blood sample.

31. The system of embodiment 20, further comprising a bidirectional flow pump that directs flow between the sample holder and the hemolyzer.

32. A method, comprising:

obtaining a whole blood sample;

placing the whole blood sample in a sample holder of a sample analyzer;

directing the whole blood sample from the sample holder to the hemolyzer;

obtaining a first light absorbance profile of the whole blood sample;

directing the hemolyzed sample of blood back to the sample holder in the sample analyzer;

hemolyzing the whole blood sample to generate a hemolyzed sample of blood;

obtaining a second light absorbance profile of the hemolyzed sample of blood; and determining a level of hemolysis in the whole blood sample by comparing the first light absorbance profile and the second light absorbance profile.

33. The method of embodiment 32, wherein directing the whole blood sample from the sample holder to the hemolyzer includes pumping the whole blood sample from the sample holder the hemolyzer with a bidirectional pump. The method of embodiment 32 also includes directing the hemolyzed sample of blood back to the sample holder in the sample analyzer includes pumping the hemolyzed sample from the sample holder back to the hemolyzer with the bidirectional pump.

34. The method of embodiment 32, further comprising: before directing the whole blood sample from the sample holder to the hemolyzer, directing the whole blood sample to a sensor module that analyze on or more analytes in the whole blood sample.

35. A system for implementing the method of embodiments 32 to the 34, comprising:

a detection unit for obtaining the first light absorbance profile of the whole blood sample and the second light absorbance profile of the hemolyzed sample of blood; and a computer processor in communication with the detection unit, the computer processor configured to execute instructions that determine the level of hemolysis of the whole blood by comparing the first light absorbance profile of the whole blood sample to the second light absorbance profile of the hemolyzed sample.

As used herein, the terms "comprises," "comprising," "includes," "including," "has," "having" or any other variation thereof, are intended to cover a non-exclusive inclusion. For example, a composition, a process, method, article, or apparatus that comprises a list of elements is not necessarily limited to only those elements but may include other elements not expressly listed or inherently present therein.

As used herein the terms "approximately," "about," "substantially" and variations thereof are intended to include not only the exact value qualified by the term, but to also include some slight deviations therefrom, such as deviations caused by measuring error, manufacturing tolerances, wear and tear on components or structures, settling or precipitation of cells or particles out of suspension or solution, chemical or biological degradation of solutions over time, stress exerted on structures, and combinations thereof, for example.

Unless expressly stated to the contrary, "or" refers to an inclusive or and not to an exclusive or. For example, a condition A or B is satisfied by anyone of the following: A is true (or present) and B is false (or not present), A is false (or not present) and B is true (or present), and both A and B are true (or present). An inclusive or may be understood as being the equivalent to: at least one of condition A or B.

In addition, use of the "a" or "an" are employed to describe elements and components of the embodiments herein. This is done merely for convenience and to give a general sense of the inventive concepts. This description should be read to include one or at least one and the singular also includes the plural unless it is obvious that it is meant otherwise.

Any reference to "one embodiment" or "an embodiment" means that a particular element, feature, structure, step, or characteristic described in connection with the embodiment is included in at least one embodiment. The appearances of the phrase "in one embodiment" in various places in the specification are not necessarily all referring to the same embodiment.

The inventive concepts disclosed herein are not limited in their application to the details of construction and the arrangement of the components or steps or methodologies set forth in the above description or illustrated in the drawings. The inventive concepts disclosed herein are capable of other embodiments or of being practiced or carried out in various ways. Also, it is to be understood that the phraseology and terminology employed herein is for the purpose of description and should not be regarded as limiting the inventive concepts disclosed and claimed herein in any way. Furthermore, numerous specific details have been set forth in order to provide a more thorough understanding of the inventive concepts. However, it will be apparent to one of ordinary skill in the art that the inventive concepts within the instant disclosure may be practiced without these specific details. In other instances, well-known features have not been described in detail to avoid unnecessarily complicating the instant disclosure.

What is claimed:

1. A method, comprising:
   obtaining a whole blood sample;
   obtaining a first light absorbance profile of the whole blood sample;
   hemolyzing the whole blood sample to generate a hemolyzed sample of blood;
   obtaining a second light absorbance profile of the hemolyzed sample of blood; and
   determining a level of hemolysis in the whole blood sample by comparing the first light absorbance profile and the second light absorbance profile, wherein the level of hemolysis is determined by:
   identifying a first contribution of constituents of the whole blood sample to the first light absorbance profile;
   identifying a second contribution of constituents of the hemolyzed blood sample to the second light absorbance profile; and
   determining the level of hemolysis based on the difference between 1) the first contribution of constituents of the whole blood sample to the first light absorbance profile, and 2) the second contribution of constituents of the hemolyzed blood sample to the second light absorbance profile; and
   wherein the constituents comprise one or more of the following: total hemoglobin (tHb), oxygen saturation of hemoglobin ($sO_2$), oxyhemoglobin ($O_2Hb$), deoxygenated hemoglobin (HHb), methemoglobin (MetHb), turbidity, total bilirubin, and combinations thereof.

2. The method of claim 1, further comprising:
   placing the whole blood sample in a sample holder of a sample analyzer;
   directing the whole blood sample to a hemolyzer before hemolyzing the whole blood sample; and
   after hemolyzing the whole blood sample, directing the hemolyzed sample of blood to the sample holder in the sample analyzer.

3. The method of claim 1, wherein obtaining the first light absorbance profile includes directing a first light signal into the whole blood sample, and wherein obtaining the second light absorbance profile includes directing a second light signal into the hemolyzed sample of blood.

4. The method of claim 1, wherein determining the level of hemolysis in the whole blood sample further includes:
   identifying at least one optical interference of the whole blood sample; and
   correcting the first light absorbance profile based on 1) the first contribution of constituents of the whole blood sample, and 2) the at least one optical interference of the whole blood sample.

5. The method of claim 4, wherein determining the level of hemolysis in the whole blood sample further includes:
   identifying at least one optical interference in the second light absorbance profile of the hemolyzed blood sample; and
   correcting the second light absorbance profile based on 1) the second contribution of the constituents of the hemolyzed blood sample, and 2) the at least one optical interference of the hemolyzed blood sample.

6. The method of claim 1, wherein determining the level of hemolysis in the whole blood sample further includes quantifying the level of hemolysis in the whole blood sample via a hemolysis model, wherein the hemolysis model outputs the level of hemolysis based on a) the first contribution of constituents of the whole blood sample to the first light absorbance profile, and b) the second contribution of constituents of the hemolyzed blood sample to the second light absorbance profile.

7. The method of claim 1, wherein determining the level of hemolysis in the whole blood sample further includes determining the level of hemolysis in the whole blood sample based on a reference module of hemolysis levels of whole blood that correspond to first and second contributions of constituents of blood to the first and second absorbance profiles, respectively.

8. The method of claim 1, wherein directing the whole blood sample to the hemolyzer includes routing the whole blood sample directly from the sample holder to the hemolyzer.

9. The method of claim 1, wherein directing the hemolyzed sample of blood to sample holder includes routing the hemolyzed sample of blood directly from the hemolyzer to the sample holder.

10. A system for analyzing components of whole blood, the system comprising:
    a detection unit for obtaining a first light absorbance profile of a whole blood sample and a second light absorbance profile of a hemolyzed sample of blood;

a hemolyzer for hemolyzing the whole blood sample into the hemolyzed sample of blood; and a computer processor in communication with the detection unit, the computer processor configured to execute instructions that determine a level of hemolysis of the whole blood by comparing the first light absorbance profile of the whole blood sample to the second light absorbance profile of the hemolyzed sample, and wherein the computer processor executes instructions that:

identify a first contribution of constituents of the whole blood sample to the first light absorbance profile;

identify a second contribution of constituents of the hemolyzed blood sample to the second light absorbance profile; and determine the level of hemolysis based on a difference between 1) the first contribution of constituents of the whole blood sample to the first light absorbance profile, and 2) the second contribution of constituents of the hemolyzed blood sample to the second light absorbance profile.

11. The system of claim 10, further comprising:

a sample holder; and a fluid handling unit including a plurality of valves, the valves configured to direct the whole blood sample from the sample holder to the hemolyzer and to the direct the hemolyzed sample of blood to the sample holder.

12. The system of claim 10, wherein the computer processor executes instructions that:

identify a first contribution of constituents of the whole blood sample to the first light absorbance profile;

identify at least one optical interference in the first light absorbance profile of the whole blood sample; and correct the first light absorbance profile based on 1) the first contribution of the constituents of the whole blood sample to the first light absorbance profile, and 2) the at least one optical interference of the whole blood sample.

13. The system of claim 12, wherein the computer processor executes instructions that:

identify a second contribution of constituents of the hemolyzed blood sample to the second light absorbance profile;

identify at least one optical interference in the second light absorbance profile of the hemolyzed blood sample; and correct the second light absorbance profile based on 1) the second contribution of the constituents of the hemolyzed blood sample, and 2) the at least one optical interference of the hemolyzed blood sample.

14. The system of claim 12, wherein the computer processor is configured to execute instructions that:

identify a first contribution of constituents of the whole blood sample to the first light absorbance profile;

identify a second contribution of constituents of the hemolyzed blood sample to the second light absorbance profile;

determine the level of hemolysis in the whole blood sample with a hemolysis model based on a) the first contribution of constituents of the whole blood sample to the first light absorbance profile, and b) the second contribution of constituents of the hemolyzed blood sample to the second light absorbance profile.

15. The system of claim 12, wherein the computer processor is configured to execute instructions that:

identify a first contribution of constituents of the whole blood sample to the first light absorbance profile;

identify a second contribution of constituents of the hemolyzed blood sample to the second light absorbance profile; and determine the level of hemolysis in the whole blood sample based on a reference module of hemolysis levels of whole blood that correspond to first and second contributions of constituents of the blood to the first and second absorbance profiles, respectively.

16. The system of claim 10, further comprising a bidirectional flow pump that directs flow between the sample holder and the hemolyzer.

* * * * *